Figure 1:
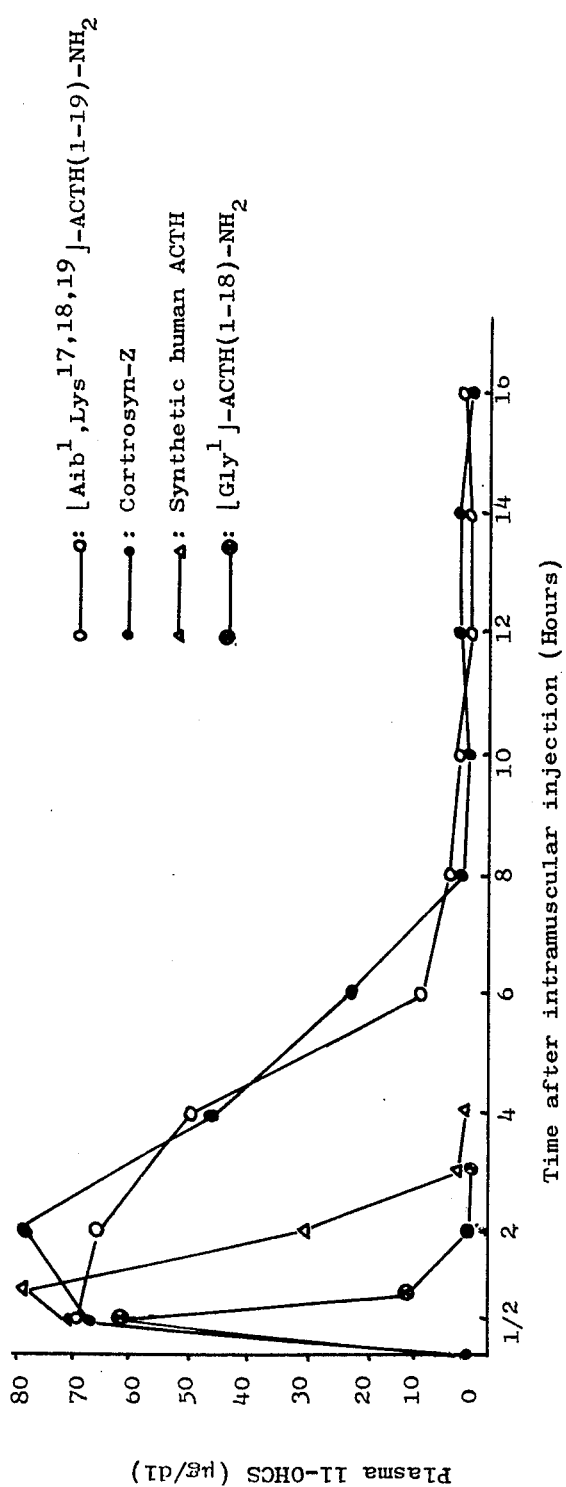

United States Patent [19]

Inouye et al.

[11] 4,018,754
[45] Apr. 19, 1977

[54] NOVEL POLYPEPTIDES HAVING ACTH-LIKE ACTION

[75] Inventors: Ken Inouye; Masaru Shin, both of Kobe; Kunio Watanabe, Otsu, all of Japan

[73] Assignee: Shionogi & Co., Ltd., Osaka, Japan

[22] Filed: July 16, 1975

[21] Appl. No.: 596,246

[30] Foreign Application Priority Data

July 30, 1974 Japan .............................. 49-87758

[52] U.S. Cl. .......................... 260/112.5 R; 424/179
[51] Int. Cl.² ............... C07C 103/52; A61K 37/40
[58] Field of Search ............................ 260/112.5 R

[56] References Cited

UNITED STATES PATENTS

| | | |
|---|---|---|
| 3,651,039 | 3/1972 | Fujino et al. ............... 260/112.5 R |
| 3,761,459 | 9/1973 | Pless et al. ................ 260/112.5 R |
| 3,761,461 | 9/1973 | Pless et al. ................ 260/112.5 R |
| 3,770,715 | 11/1973 | Tesser et al. ............... 260/112.5 R |
| 3,792,033 | 2/1974 | Iselin et al. ................ 260/112.5 R |
| 3,873,511 | 3/1975 | Otsuka et al. .............. 260/112.5 R |

Primary Examiner—Lewis Gotts
Assistant Examiner—Reginald J. Suyat
Attorney, Agent, or Firm—Wenderoth, Lind & Ponack

[57] ABSTRACT

A polypeptide of the formula:

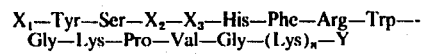

wherein $X_1$ is α-aminoisobutyric acid, β-alanine, L-serine, D-serine, glycine, D-alanine, γ-aminobutyric acid or sarcosine residue; $X_2$ is L-methionine, L-norleucine, L-isoleucine or L-norvaline residue; $X_3$ is L-glutamic acid or L-glutamine residue; $n$ is an integer of 5–10; and Y is —$R_1$,

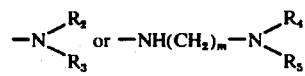

wherein $R_1$ is hydroxy or lower alkoxy having 1–5 carbon atoms; $R_2$, $R_3$, $R_4$ and $R_5$ are each hydrogen or lower alkyl having 1–5 carbon atoms; $m$ is an integer of 1–10 and Y is a group bound to the carbonyl group of the C-terminal lysine residue; non-toxic acid addition salts thereof; and complexes thereof; being useful as a medicament owing to their strong adrenal-stimulating activity with protracted action and little side effects. They can be prepared by condensing the amino acids together one by one or by condensing the small peptide fragments together in a per se conventional manner.

5 Claims, 2 Drawing Figures

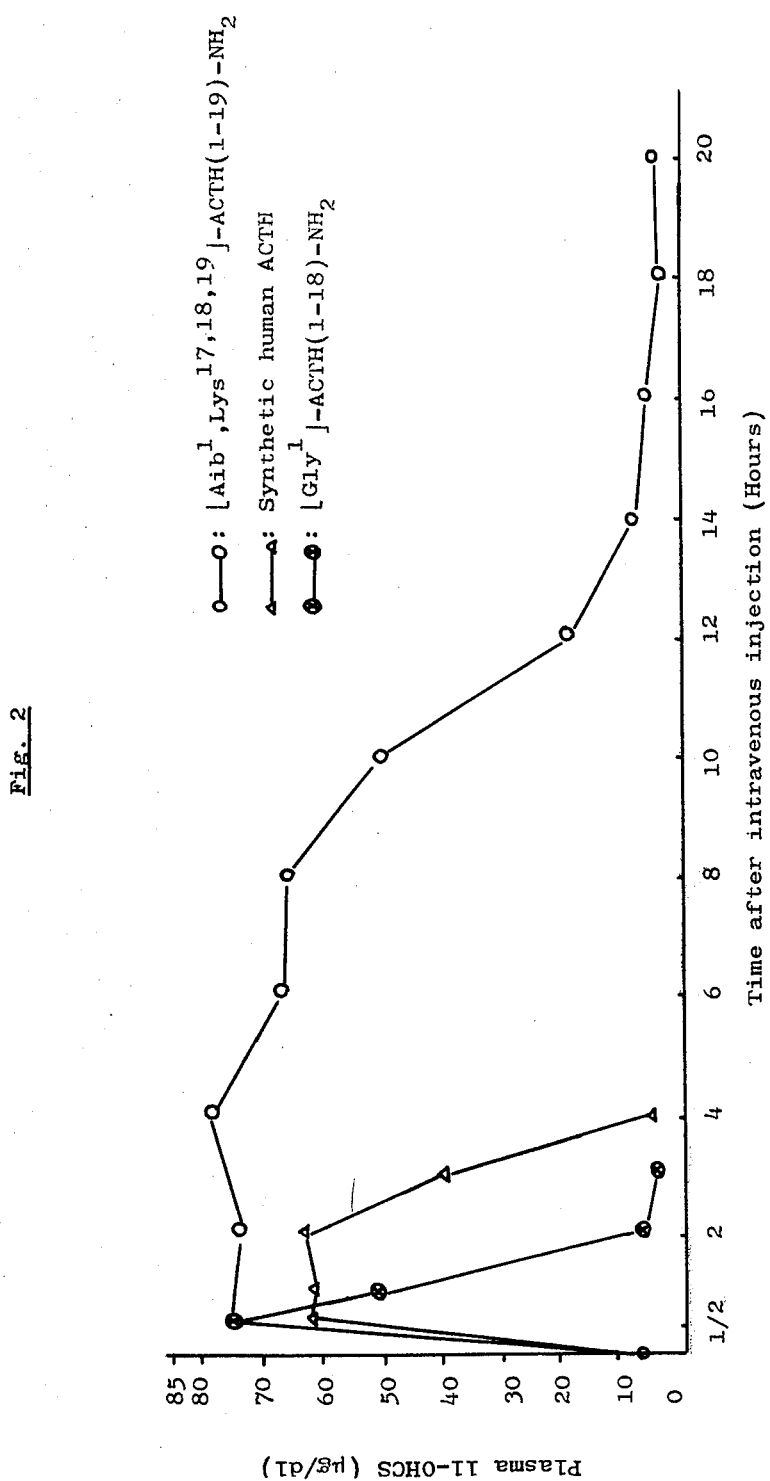

NOVEL POLYPEPTIDES HAVING ACTH-LIKE ACTION

This invention relates to novel polypeptides having strong ACTH-like action, particularly adrenal-stimulating activity, with protracted action and little side effects; non-toxic acid addition salts thereof and complexes thereof; and to a process for the production of the same. The polypeptides of the invention can be represented by the formula:

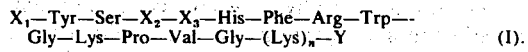   (I).

wherein $X_1$ is α-aminoisobutyric acid, β-alanine, L-serine, D-serine, glycine, D-alanine, γ-aminobutyric acid or sarcosine residue; $X_2$ is L-methionine, L-norleucine, L-isoleucine or L-norvaline residue; $X_3$ is L-glutamic acid or L-glutamine residue; $n$ is an integer of 5–10; and Y is $-R_1$,

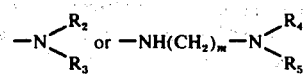

wherein $R_1$ is hydroxy or lower alkoxy having 1–5 carbon atoms (e.g., methoxy, ethoxy, propoxy); $R_2$, $R_3$, $R_4$ and $R_5$ are each hydrogen or lower alkyl having 1–5 carbon atoms (e.g., methyl, ethyl, propyl); $m$ is an integer of 1–10 and Y is a group bound to the carbonyl group of the C-terminal lysine residue.

Up to the present, a number of modified ACTH peptides which possess chain lengths shorter than that of native hormone (ACTH) and exhibit ACTH-like action have been reported. Such modifications are directed mainly to the positions 1,4,5,15, 16, 17, 18 and to their C-terminal residue. For example, the first amino acid L-serine can be substituted by α-aminoisobutyric acid, β-alanine, D-serine, glycine, D-alanine, γ-aminobutyric acid or sarcosine; the fourth amino acid L-methionine by L-norleucine, L-isoleucine or L-norvaline; the fifth amino acid L-glutamic acid by L-glutamine, the 15 and the 16 amino acids L-lysines by L-ornithines; the 17 and the 18 amino acids L-arginines by L-lysines or L-ornithines; and the carboxyl group of the C-terminal amino acid is in the form of amide. However, one of the drawbacks of these peptides is that they exhibit rather strong melanocyte-stimulating activity compared to their adrenal-stimulating activity. Since all the corticotropically active polypeptides contain in the molecule the amino acid sequence responsive for the melanocyte stimulating activity, they exhibit more or less such undesirable activity. Thus, when patients receive such peptide having strong melanocyte-stimulating activity, the skin of patients is darkened.

In addition, when corticotropically active peptides are used as a drug for therapeutical purposes, they are administered in the form of a complex with zinc. The reason that said complexes have been employed in the art consists in that they show protracted action, compared to the corresponding plain peptide. However, several reports have been recently published to indicate that a dangerous anaphylactic reaction may be caused by such a complex of ACTH with zinc, more frequently than by the plain peptide. In this respect, a plain peptide having a strong adrenal-stimulating action at a high activity level is quite desirable from its therapeutical view point.

Further, the peptide is also desirable to be a weak melanocyte-stimulating agent.

In the course of the investigations to solve the above problems of corticotropically active polypeptides, the present inventors have discovered that, in addition to the modifications of the amino acid residues at positions 1, 17, and 18 of the peptide, further replacement at positions 19–24 by lysine residues improves its biological properties greatly resulting in the enhancement of potency and the prolongation of action with little side effects. The amino acid sequence 15 to 24 of native corticotropin is [15]Lys—Lys—Arg—Arg—Pro—Val—Lys—Val—Tyr—Pro[24]. There is no report on the substitution experiment at positions 15–24 in ACTH. The present invention is based on these observations.

According to the invention, the desired polypeptides (I) can be prepared by condensing the amino acids together one by one or by condensing the small peptide fragments together in a per se conventional manner. More particularly, they can be prepared by (a) condensing an amino acid ester or peptide ester having a free amino group with other amino acid or peptide having protected amino group(s) in the presence of a condensing agent (e.g., dicyclohexylcarbodiimide, carbonyldiimidazole), or (b) reacting an amino acid or peptide having a free amino group and protected or unprotected carboxyl group(s) with other amino acid or peptide having an activated carboxyl group and protected amino group(s), and removing the protecting groups from the resulting protected peptide by catalytic hydrogenolysis, acid solvolysis, hydrolysis, hydrazinolysis, sodium in liquid ammonia reduction or other means.

Peptide-bonds are formed by the usual methods. Examples of said methods are the azide method, the dicyclohexylcarbodiimide method, the carbonyldiimidazole method, the mixed anhydride method, the activated ester method (e.g., p-nitrophenyl ester method, N-hydroxysuccinimide ester method, cyanomethyl ester method, p-nitrophenyl thiol ester method, pentachlorophenyl ester method), the isoxazolium method, the N-carboxyanhydride method and the like. The desired peptides are also prepared by the so-called solid phase peptide synthesis or by the oxidation-reduction method. Although above-mentioned methods can be employed for the formation of any peptide bond in preparing the present polypeptides, the most commonly practiced methods are the dicyclohexylcarbodiimide method, the azide method, the mixed anhydride method and the activated ester method. In the coupling reaction mentioned above, N-hydroxysiccinimide, N-hydroxy-5-norbornene-2,3-dicarboxyimide or 1-hydroxybenzotriazole may be added.

In the production of the desired polypeptides (I), any free functional groups not participating in the reaction are advantageously protected, especially by such groups that can be easily removed by catalytic hydrogenolysis, acid solvolysis, hydrazinolysis, hydrolysis, or sodium in liquid ammonia reduction. The carboxyl group is advantageously protected by esterification, for example, with a lower alkanol (e.g., methanol, ethanol, propanol, t-butanol) or an aralkanol (e.g., benzyl alcohol, P-nitrobenzyl alcohol, p-methoxybenzyl alcohol). These carboxyl-protecting groups are introduced by the usual method.

The amino group is protected preferably by introducing a group such as 1-methylcyclohexyloxycarbonyl group, 1-methylcyclopentyloxycarbonyl group, 9-methyl-9-fluorenyloxycarbonyl group, t-butyloxycarbonyl group, t-amyloxycarbonyl group, o-nitrophenylsulphenyl group, 2-(p-diphenyl)isopropyloxycarbonyl group, benzyloxycarbonyl group, tosyl group, formyl group or trityl group, in a conventional manner. For the protection of the guanidyl group of arginine, nitro group, tosyl group or adamantyloxycarbonyl group is preferably used, but the protection of the guanidyl group is not always necessary. The $\epsilon$-amino group of lysine is advantageously protected by such amino-protecting groups as those mentioned above. However, it is desirable to choose an $\omega$-amino protecting group which is selectively removable from that of $\alpha$-amino protecting group. The $\gamma$-carboxyl group of glutamic acid is preferably protected by such carboxyl-protecting groups as mentioned above and the imidazole group of histidine may be protected by tosyl group, benzyloxycarbonyl group, benzyl group or the like. Further, the hydroxy group of serine or tyrosine may be protected by acetyl group, benzyl group or t-butyl group, but such protection is not always necessary.

Removal of the protecting group from the amino acids, the intermediate fragments or from the polypeptides in the last stage is carried out in a per se conventional manner employed in the field of peptide chemistry. Examples of such methods are reduction, catalytic hydrogenolysis, sodium in liquid ammonia reduction, acid solvolysis using an acid (e.g., hydrogen fluoride, hydrogen bromide, hydrogen chloride, hydrobromic acid, hydrochloric acid, trifluoroacetic acid, acetic acid, formic acid) and acid hydrolysis and saponification with an alkali (e.g., sodium hydroxide).

The final coupling reaction for producing the desired polypeptides (I) is performed, for example, by condensing a protected decapeptide of the formula:

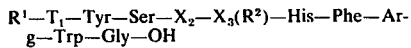

wherein $R^1$ is an amino-protecting group and $R^2$ is a protecting group for the $\gamma$-carboxyl group of glutamic acid and $X_1$, $X_2$ and $X_3$ have each the same meaning as defined above, with a protected peptide of the formula:

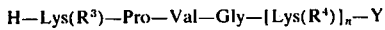

wherein $R^3$ and $R^4$ are each an $\epsilon$-amino-protecting group, and Y and $n$ have each the same meaning as defined above, by the activated ester method, the azide method, the dicyclohexylcarbodiimide method, the carbonyldiimidazole method, the mixed anhydride method or combination method thereof; and removing all the protecting groups from the resultant protected peptide of the formula:

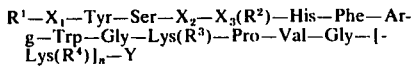

wherein all the symbols have each the same meaning as defined above, by acid solvolysis, catalytic hydrogenolysis, hydrazinolysis or sodium in liquid ammonia reduction.

The final coupling reaction is preferably carried out by the activated ester method, particularly the N-hydroxysuccinimide ester method, in an inert solvent at a temperature of $-20°$ to $60°$ C, especially $0°$ to $45°$; C, for about 1 hour to 72 hours, especially for about several hours to 48 hours. Examples of the solvent used are dimethylformamide, dimethylsulfoxide, hexamethylphosphortriamide, and an aqueous solvent thereof, and a mixed solvent thereof. The protecting groups are removed preferably by acid solvolysis using an acid such as hydrogen halide (e.g., hydrogen fluoride, hydrogen bromide, hydrogen chloride) or trifluoroacetic acid at $-20°$ to $60°$ C for 30 minutes to several hours.

The polypeptides prepared by the present invention can be purified by ion-exchange chromatography, partition chromatography, exlusion chromatography, or by adsorption chromatography on a column of ion-exchange resin, ion-exchange cellulose, cellulose, cross-liked dextran gel (e.g., Sephadex), polyacrylamide gel (e.g., Bio-Gel P), silica gel, or other suitable material, countercurrent distribution method or by other suitable methods usually used in the field of peptide chemistry.

The novel polypeptides of the invention are produced in the form of a free base or its salt, depending on the purification processes used. Naturally, the salts can be converted into the free base, and to the contrary, the free base can be converted into the acid addition salt by treatment with a suitable acid in a conventional manner. Examples of the acid are inorganic acids such as hydrohalic acid (e.g., hydrochloric acid, hydrobromic cid) or phosphoric acid, and organic acids such as formic acid, acetic acid, propionic acid, succinic acid, citric acid, benzenesulfonic acid or p-toluenesulfonic acid. An equimolar or excess amount of acid may be used in such salt formation.

The polypeptides of the present invention can be converted into the corresponding complex with a complex-forming heavy metal (e.g., zinc, copper, iron, nickel, cobalt) or a complex-forming polyamino acid (e.g., poly-glutamic acid, polyaspartic acid, copolyglutamyl-tyrosine, copoly-aspartyl-glutamic acid) in a per se conventional manner. The complex thus obtained shows long-lasting action.

The polypeptides of the present invention show excellent biological properties, and such properties are superior to those of native corticotropin and those of the related known peptides.

Assays for adrenal-simulating activity of the present polypeptides were carried out, comparing with that of native corticotropin (ACTH), [Gly$^1$]—ACTH(1-18-)—NH$_2$ (Bull. Chem. Soc. Japan 43, 196 (1970)), [Aib$^1$]—ACTH(1-18)—NH$_2$ (ibid., 43, 3873 (1970)), [Aib$^1$,Lys$^{17,18}$]—ACTH(1-18)—NH$_2$, Cortrosyn$^R$(N. V. Organon, Netherland), and Cortrosyn$^R$—Z. The adrenal-stimulating activity by the intravenous administration to hypophysectomized rat was determined in such a manner that a peptide preparation was injected into the femoral vein and a blood sample was collected from the abdominal aorta 30 minutes after the injection. The adrenal-stimulating activity by the intramuscular administration to hypophysectomized rat was also determined, where a peptide preparation was injected into the thigh muscle and a blood sample was collected from the abdominal aorta 30 minutes after the injection. Throughout the experiment, the USP Corticotropin Reference Standard was used as a standard and the production of 11-hydroxycorticosteroids was determined by the fluorophotometric method of Peterson [J. Biol. Chem. 225 25 (1975)]. For each assay method several determinations were usually performed and the data obtained independently were submitted to the statistical treatment by Sheps and Moore procedure [J. Pharmacol. Extl. Therap. 128 99 (1960)].

The effect on adrenal growth and thymus involution was determined in the following manner: peptides were intramuscularly injected into rats weighing 100–150 g at a dose of 20μg and 100 μg/rat/day for 2 days, respectively. The rats were then submitted to autopsy 24 hours after the last injection, and then the adrenal and thymus were weighed respectively.

The in vivo melanocyte-stimulating activity was determined according to the method of A. Tanaka described in Endocrinol. Japonica 19, 383 (1972).

The test results on biological properties are shown in the following table.

Table 1

| Peptide | Adrenal-stimulating activity | | effect on adrenal growth and thymus involution[a] | Melano-cyte-stimu-lating activity in vivo[b] | a/b |
|---|---|---|---|---|---|
| | i.v. | i.m. | | | |
| [Aib$^1$,Lys$^{17,18,19}$]-ACTH(1–19)-NH$_2$ | 5.7 | 7.8 | 0.41 | 0.11 | 3.73 |
| [Aib$^1$,Lys$^{17,18,19,20}$]-ACTH(1–20)-NH$_2$ | 6.3 | 10.7 | 0.18 | 0.15 | 1.20 |
| Native ACTH | 1.0 | 4.0 | * | | |
| [Gly$^1$]-ACTH(1–18)-NH$_2$ | 1.0 | 1.0 | * | 0.11 | |
| [Aib$^1$]-ACTH(1–18)-NH$_2$ | 4.1 | 9.9 | 0.12 | 1.00 | 0.12 |
| [Aib$^1$,Lys$^{17,18}$]-ACTH(1–18)-NH$_2$ | 9.3 | 9.4 | 0.40 | 0.82 | 0.49 |
| Cortrosyn | 1.8 | 3.1 | * | | |
| Cortrosyn-Z | | | | 1.00 | 1.72 | 0.58 |

Note: *The effects on adrenal growth and thymus involution are very weak. Cortrosyn$^R$ = ACTH(1–24)-NH (N.V.Organon, Netherlands), Cortrosyn$^R$-Z = Zinc complex of Cortrosyn (N.V. Organon, Netherlands). The adrenal-stimulating activity and melanocyte-stimulating activity are expressed in terms of the relative potency.

There are several methods for determining the adrenal-stimulating activity which is the main role of ACTH, and the most reliable method for the examination of such activity is, among others, a test method which studies the effect on adrenal growth and thymus involution. Thus, it can be said that the polypeptides having a higher ratio of a/b (a=effect on adrenal growth and thymus involution, b=melanocyte stimulating activity) are desirable. It is to be noted that the effects of native ACTH, [Gly$^1$]—ACTH(1–18)—NH$_2$ and Cortrosyn on adrenal growth and thymus involution are very weak. These peptides may not be suitable as a drug for practical use. As clearly shown in the above table, the polypeptides of the invention is superior to native ACTH and known peptides, in view of its high ratio of a/b.

The protracted action of the present polypeptides, e.g., [Aib$^1$,Lys$^{17,18,19}$]—ACTH(1–19)—NH$_2$, was studied using rats weighing 100–120 g. Synthetic human ACTH, Cortrosyn—Z$^R$ (zinc complex suspension of ACTH(1–24)—OH) and [Gly$^1$]—ACTH(1–18)—NH$_2$ were used for comparison. The petides were intramuscularly or intravenously injected into rats at a dose of 5 μg/rat, and then the production of 11-hydroxycorticosteroids (11-OHCS) was determined. Time course of 11-OHCS level in the plasma when the peptides were administered intramuscularly and intravenously is shown in FIG. 2, respectively. As can be seen from the figures, [Aib$^1$, Lys$^{17,18,19}$]—ACTH(1–19)—NH$_2$ of the present invention shows very protracted action, compared to synthetic human ACTH and related peptides.

Cortrosyn-Z is the only ACTH preparation which has been used for therapeutical purpose, though it has rather strong melanocyte stimulating activity (c.f. Table 1). The adrenal-stimulating action of [Aib$^1$, Lys$^{17,18,19}$]—ACTH(1–19)—NH$_2$ is protracted to almost the same extent as that produced by Cortrosyn-Z. Since [Aib$^1$, Lys$^{17,18,19}$]—ACTH(1–19)—NH$_2$ itself, not in the form of a complex with zinc, manifests such long-lasting action, the peptides of the invention is very valuable for therapeutical use. In FIG. 2, Cortrosyn-Z (suspension of a zinc complex of ACTH(1–24)—OH) is not shown, because the suspension cannot be used through intravenous route.

The polypeptides of the invention are highly useful and advantageous for therapeutical purposes, e.g., in the treatment of varied inflammations, adrenal insufficiency due to pituitary disorder, acute or chronic articular rheumatisms, allergic diseases or adrenarches of human beings and domestic animals, or for testing the adrenocortical function of animals and human beings.

The polypeptides, the acid addition salts and the complexes can be administered orally or parenterally in per se conventional forms, e.g., injection, liquid, suspension, emulsion, or aerosol, optionally with suitable carriers, stabilizers, emulsifiers, preservatives, buffers, isotonizing agents and/or wetting agents, where a therapeutically active amount of the active ingredient is contained.

Thus, the present invention includes a pharmaceutical or veterniary preparation comprising a compound in accordance with the invention and an inert pharmaceutical excipient.

The effective dose can be easily determined by a physician on the basis of the data herein-described. Thus, a typical clinical dosage range for the polypeptides of the invention is approximately 0.001 mg/kg to 0.02 mg/kg per day for a normal adult. The present polypeptides are advantageously administered in injections as a dosage form, and administration is repeated as often as required in accordance with the physician's indication.

The abbreviated designation of amino acids, peptides and their derivatives used in the present specification and claims accords with the proposals of the IUPAC-IUB Commission of Biochemical Nomenclature [J. Biol. Chem. 241, 2491 (1966), ibid. 242, 555 (1967), ibid, 247 977 (1972)]. All the amino acid residues are of the L-configuration, unless otherwise indicated.

The analogs of an ACTH peptide comprising the amino acid residues in positions m through n (as numbered from N-terminal) are designated for abbreviation as X—[A$^i$, B$^j$, . . .]—ACTH (m–n)—Y where [A$^i$, B$^j$, . . .] denotes substitutions by A, B, . . . for the amino acid residues in positions i, j, . . . and X and Y are the hydrogen or its substituent of N-terminal α-amino group and the hydroxyl or its substituent of C-terminal α-carboxyl group, respectively. When X means hydrogen itself the symbols H may be omitted.

The following examples are given solely for the purpose of illustration and are not to be construed as limitation of the invention.

EXAMPLE 1

Preparation of Aib—Tyr—Ser—Met—Glu—His—Phe—Arg—Trp—Gly—Lys—Pro—Val—Gly—Lys—Lys—Lys—Lys—Lys—NH$_2$ [Aib$^1$, Lys$^{17,18,19}$]-ACTH(1–19)—NH$_2$). (Aib=α—aminoisobutyric acid).

(i). Z—Lys(Boc)—NH₂ (Z=benzyloxycarbonyl, Boc=t–butyloxycarbonyl).     (I)

To a solution of N^α-benzyloxycarbonyl=N^ε-t-butyloxycarbonyl-L-lysine N-hydroxysuccinimide ester (Z-Lys(Boc)—OSu, 9,55 g) in dioxane (50 ml) is added 10 ml of conc. ammonia. The mixture is stirred at room temperature for 2 hours. After evaporation, the crystalline residue is extracted with ethyl acetate. The extract is washed with cold 0.5N hydrochloric acid, water, M sodium bicarbonate solution, and water, dried over anhydrous sodium sulfate, and concentrated in vacuo. The residue is crystallized from ethyl acetate and petroleum ether. Yield 7.18 g (94.6%), mp. 145°–146° C, $[\alpha]_D^{23.5}$ −2.1±0.5° Cc 1.004, methanol).

Anal. Calcd. for $C_{19}H_{29}N_3O_5$: C, 60.14; H, 7.70; N, 11.07. Found: C, 60.42; H, 7.61; N, 11.00 ii. H—Lys(Boc)—NH₂     II

Z—Lys(Boc)—NH₂ (5.69 g) is hydrogenolyzed over palladium-black catalyst for 2.5 hours in methnol (50 ml). The catalyst is removed by filtration and washed with methanol. The combined filtrate and washings are evaporated in vacuo. The oil residue is solidified in petroleum ether, collected by filtration, and dried in vacuo. Recrystallization from ethyl acetate and petroleum ether gives 3.61 g (98.1%) of the desired product, mp. 104°–105.5° C, $[\alpha]_D^{23.5}$ +8.2±0.5° (c 1.006, methanol).

Anal. Calcd. for $C_{11}H_{23}N_3O_3$: C, 53,86; H, 9.45; N, 17.13. Found: C, 53.89; H, 9.54; N, 17.02.

iii. Z—Lys(Boc)—Lys(Boc)—NH₂     III

A solution of Z—Lys(Boc)—OSu (4.78 g) in chloroform (20 ml) is added to a solution of H—Lys(Boc)—NH₂ (2.45 g) in ethyl acetate (30 ml). The mixture is stirred at room temperature for 1 hour. Methanol (20 ml) is added and stirring is continued for 3 hours. The reaction mixture is concentrated in vacuo. The residue is suspended in ethyl acetate, and washed successively with cold 0.5N hydrochloric acid, water, M sodium bicarbonate, and water. The ethyl acetate insoluble materials are collected by filtration, washed and dried in vacuo. Yield 5.15 g, mp. 168°–169° C. The filtrate and washings are combined and evaporated to give crystalline materials. This residue and the ethyl acetate insoluble materials are combined and recrystallized from methanol and ether. Yield 5.25 g (86.2%), mp. 169°–170° C, $[\alpha]_D^{22.5}$ −11.1±0.3° (c 2.025, methanol).

Anal. Calcd. for $C_{30}H_{49}N_5O_8$: C, 59.29; H, 8.13; N, 11.52. Found: C, 59.28; H, 8.12; N, 11.52 iv. H—Lys(Boc)—Lys(Boc)—NH₂     IV

Z-Lys(Boc)—Lys(Boc)—NH₂ (4.25 g) is hydrogenolyzed over palladium black catalyst for 2.5 hours in methanol (50 ml). After removal of the catalyst by filtration, the filtrate is evaporated in vacuo to give a crystalline residue. Recrystallization from ethyl acetate and n-hexane give 3.30 g (99.4%) of the desired product, mp. 112°–115° C. $[\alpha]_D^{22.5}$ −27.2±0.4° (c 2.023, chloroform).

Anal. Calcd. for $C_{22}H_{43}N_5O_6$: C, 55,79; H, 9.15; N, 14.79. Found: C, 55.75; H, 9.14; N, 14.85.

v. Z-Lys(Boc)—Lys(Boc)—Lys(Boc)—NH₂     V

To a solution of H—Lys(Boc)—Lys(Boc)—NH₂ (2.84 g) in chloroform (50 ml) is added Z—Lys(-Boc—OSu (2.87 g). The mixture is stirred at room temperature for 68 hours. After evporation, the residue is dissolved in ethyl acetate. The solution is washed with cold 0.1N hydrochloric acid, water, M sodium bicarbonate solution, and water, and evaporated in vacuo. The residue is redissolved in ethyl acetate and kept in a refrigerator. The gel-like precipitates are collected, washed, and dried in vacuo at 60° C to give the desired product. Yield 4.85 g (96.6%), mp. 170°–171° C, $[\alpha]_D^{23.5}$ −16.1±0.6° (c 1.034, methanol).

Anal. Calcd. for $C_{41}H_{69}N_7O_{11}$: C, 58.90; H, 8.32; N, 11.73. Found: C, 58.78; H, 8.32; N, 11.47.

vi. H—Lys(Boc)—Lys(Bos)—Lys(Boc)—NH₂     VI

Z—Lys(Boc)—Lys(Boc)—Lys(Boc)—NH₂ (3.34 g) is hydrogenolyzed over palladium black catalyst for 2 hours in methanol (50 ml). After removal of the catalyst by filtration, the filtrate is evaporated in vacuo to give a residue, which is dissolved in ethyl acetate and precipitated by adding petroleum ether. The precipitates are collected, washed and dried in vacuo at 60° C to give the desired product. Yield 2.80 g, (99.6%), mp. 114°–117° C, $[\alpha]_D^{23}$ −4.2±0.5° (c 1.018, methanol).

Anal. Calcd. for $C_{33}H_{63}N_7O_9$: C, 56.47; H, 9.05; N, 13.97. Found: C, 56.46; H, 9.08; N, 13.83.

vii. Z—Lys(Boc)—Lys(Boc—Lys(Boc—Lys(Boc)—NH₂     VII

Z—Lys(Boc)—OSu (1.43 g) is added to a solution of H—Lys(Boc)—Lys(Boc)—Lys(Boc)—NH₂ (2.11 g) in chloroform (30 ml) and methanol (3 ml). The mixture is allowed to stand at room temperature for 3 hours and then evaporated in vacuo. The residue is taken into ethyl acetate, and washed successively with cold 0.1N hydrochloric acid, water, M sodium bicarbonate, and water, and concentrated to dryness in vacuo. The solid residue is precipitated from methanol and ether, and is collected by suction, washed, and dried at 60° C to give the desired product. Yield 3.04 g(95.3%), mp. 194°–195° C, $[\alpha]_D^{23.5}$ −18.6±0.6° (c 1.012, methanol).

Anal. Calcd. for $C_{52}N_{89}N_9O_{14}$: C, 58.68; H, 8.43; N, 11.84. Found: C, 58.89; H, 8.73; N, 11.84.

viii. H-Lys(Boc)—Lys(Boc)—Lys(Boc)—Lys(Boc)—NH₂     VIII

Z—Lys(Boc)—Lys(Boc)—Lys(Boc)—Lys(Boc)—NH₂ (2.13 g) is hydrogenolyzed over palladium black catalyst for 4.5 hours in methanol (30 ml). After filtration and evaporation, the residue is precipitated from methanol and ethyl acetate. The gel-like precipitates are filtered, washed, and dried at 60° C. Yield 1.64 g (88.1%), mp. 168°–170° C, $[\alpha]_D^{24}$ −11.9±0.6° (c 1.006, methanol).

Anal. Calcd. C, 56.81; H, 8.94; N, 13.55. Found: C, 56.94; H, 8.94; N, 13.55.

ix. Z—Lys(Boc)—Lys(Boc)—Lys(Boc)—Lys(Boc)—Lys(Boc)—NH₂     IX

Z—Lys(Boc)—OSu (430 mg) and H—Lys(Boc)—Lys(Boc)—Lys(Boc)—Lys(Boc)—NH₂ (837 mg) are allowed to react at room temperature in dimethylformamide (3 ml) overnight. Ice-cold 0.1N hydrochloric acid (10 ml) is added into the reaction mixture. The crystalline precipitates are collected, washed with water and ether, and dried in vacuo. Recrystallization from aqueous methanol gives 1.08 g (92.8%) mp. 223°–224° C, $[\alpha]_D^{23}$ −20.4±0.6° (c 0.957, methanol).

Anal. Calcd. for $C_{63}H_{109}N_{11}O_{17}$: C, 58.54; H, 8.50; N, 11.92. Found: C, 58.71; H, 8.55; N, 11.78.

x.  H—Lys(Boc)—Lys(Boc)—Lys(Boc)—Lys(Boc)—Lys(Boc)—NH$_2$      X

Z—Lys(Boc)—Lys(Boc)—Lys(Boc)—Lys(Boc)—Lys(Boc)—NH$_2$ (905 mg) is hydrogenated over palladium-black catalyst for 4.5 hours in methanol (20 ml). The catalyst is removed by filtration and washed with methanol. The combined filtrate and washings are concentrated in vacuo to give solid residue, which is precipitated from methanol and ether. Yield 836 mg. mp. 208°–210° C, $[\alpha]_D^{23}$−17.±0.6° (c 1,029, methanol).

Anal. Calcd. for $C_{55}H_{103}N_{11}O_{15}$: C, 55.30; H, 9.03; N, 12.90. Found: C, 55.37; H, 8.78; N, 12.97.

xi.  Z—Lys(Boc)—pro—Val—Gly—Lys(Boc)—Lys(Boc)—Lys(Boc)—Lys(Boc)—Lys(Boc)—NH$_2$      XI To a solution of Z—Lys(Boc)—Pro—Val—Gly—OH (209 mg) (prepared according to the method as described in Japanese patent publication No. 2545/1973), N-hydroxysuccinimide (38 mg) and H—Lys(Boc)—Lys(Boc)—Lys(Boc)—Lys(Boc)—Lys(Boc)—NH$_2$ (348 mg) in dimethylformamide (6 ml) is added at −10° C N,N′-dicyclohexylcarbodiimide (68 mg). After stirring at 5° C for 20 hours and at room temperature for 24 hours, dicylcohexylurea is removed by filtration. The filtrate is concentrated to give gel-like residue. This residue is tritulated in ethyl acetate, collected, and dried in vacuo. Yield 469 mg (88.2%). mp. 234°–235° C, $[\alpha]_D^{24.5}$ −29.5±0.7° (c 1,005, methanol).

Anal. Calcd. for $C_{86}H_{148}N_{16}O_{23}$: C, 58.22; H, 8.41; N, 12.63. Found: C, 58.46; H, 8.54; N, 12.49.

xii.  Aib—Tyr—Ser—Met—Glu—His—Phe—Arg—Trp—Gly—Lys—Pro—Val—Gly—Lys—Lys—Lys—Lys—Lys—NH$_2$   ([Aib$^1$, Lys$^{17,18,19}$]—ACTH(1-19)—NH$_2$)      XII Boc—Aib—Tyr—Ser—Met—Glu(OBu$^t$)—His—Phe—Arg-Trp—Gly—OH.HCl (100 mg) (prepared according to the method as described in Japanese patent publication No. 2545/1973 or Japanese patent application No. 46147/1974, Japanese unexamined patent publication No. 140444/1975) is coupled with H—Lys(Boc—Pro—Val—Gly—Lys(Boc)—Lys(Boc)—Lys(Boc)—Lys(Boc)—Lys(Boc)—NH$_2$ (0.06 mmole) (obtained from the carbobenzoxy derivative (xi) by catalytic hydrogenation) in a mixture of dimethylformamide and dimethylsulfoxide (1:1 by volume) (4 ml) in the presence of N-hydroxysuccinimide (15 mg), triethylamine (0.01 ml) and N,N′-dicyclohexylcarbodiimide (54.5 mg). After 21 hours the reaction mixture is added in a mixture of ethyl acetate and ether (1:1, 15 ml). The precipitates are collected, washed, and dried in vacuo (153 mg). This peptide is treated with 90% aqueous trifluoroacetic acid (2 ml) in the presence of ethanedithiol (0.1 ml) and anisole (0.1 ml). After 1 hour at room temperature, the precipitates which formed by adding ether (10 ml) are filtered, washed, and dried (168 mg). The nonadecapeptide trifluoroacetate is dissolved in 0.1N acetic acid and passed through a column of Amberlite CG-400 (acetate form, 0.9 × 25 cm). The peptide acetate solution is concentrated and lyophilized (125 mg). Purification by on a column of carboxymethyl cellulose is done: Serva CM-cellulose, 0.70 meq/g, 2.2 × 25 cm, flow rate 150 ml/hr, ammonium acetate buffer, pH 6.80, 0.03–0.60 linear gradient elution. The tubes (Nos. 101–158,10 ml/tube) are pooled, evaporated and lyophilized (89 mg). Further purification is done by partition chromatography: column; 2.0 × .75 cm, Sephadex G-25 solvent; n-butanol/acetic acid/pyridine/water=12:3:4:6 (v/v), flow rate; 15 ml/hr, detection; Folin-Lowry procedure. The tubes (Nos. 60–100, 5 ml/tube) are pooled, evaporated, and lyophilized. Yield 69 mg, $[\alpha]_D^{24.5}$ −64.4±2.1° (c 0.511, N/10 acetic acid), $\lambda_{max}^{0.1NaOH}$ 282 mμ ($E_{1\%}^{1\ cm}$ 25.1), 289 mμ ($E_{1\%}^{1\ cm}$ 23.8), $\lambda_{max}^{0.1N\text{-}HCl}$ 280 mμ ($E_{1\%}^{1\ cm}$ 22.1), $\lambda_{shoulder}^{0.1N\text{-}HCl}$ 288 mμ ($E_{1\%}^{1\ cm}$ 16.7). Amino acid analysis (molar ratio): Lys 5.92 (6), His 1.00 (1), Arg 0.96 (1), Ser 0.89 (1), Glu 1.10 (1), Pro 1.14 (1), Gly 2.00 (2), Aib 0.77 (1), Val 0.99 (1), Met 1.02 (1), Tyr 1.03 (1), Phe 1.03 (1), Trp/Tyr1.13 (1). The value in the parenthesis means the theoretical molar ratio.

EXAMPLE 2

Preparation of Aib—Tyr—Ser—Met—Glu—His—Phe—Arg—Trp—Gly—Lys—Pro—Val—Gly—Lys—Lys—Lys—Lys—Lys—Lys—NH$_2$ ([Aib$^1$, Lys$^{17,18,19,20}$]—ACTH(1-20)—NH$_2$ xiii.  Z-Lys(Boc)—Lys(Boc)—Lys(Boc)—Lys(Boc)—Lys(Boc)—Lys(Boc)—NH$_2$      (XIII)

Z—Lys(Boc)—OSu (167 mg) and H—Lys(Boc)—Lys(Boc)—Lys(Boc)—Lys(Boc)—Lys(Boc)—NH$_2$ (418 mg) are dissolved in dimethylformamide (3 ml) and allowed to react at room temperature for 20 hours. After addition of ice-cold 0.1N hydrochloric acid (10 ml) into the reaction mixture, the precipitates are collected by filtration, washed with water, and dried in vacuo. Yield 530 mg (99.6%), mp 231.5°–233° C. Recrystallization from aqueous methanol gives 514 mg, (96.6%), mp. 229°–230° C, $[\alpha]_D^{23}$ −20.8±0.6° (c 1.042, methanol).

Anal. Calcd. for $C_{74}H_{129}N_{13}O_{20}$: C, 58.53; H, 8.53; N, 11.83. Found: C, 58.44; H, 8.55; N, 11.97.

xiv.  Aib—Tyr—Ser—Met—Glu—His—Phe—Arg—Trp—Gly—Lys—Pro—Val—Gly—Lys—Lys—Lys—Lys—Lys—Lys—NH$_2$      (XIV)

To a solution of Boc—Aib—Tyr—Set—Met—Glu(OBu$^t$)—His—Phe—Arg—Trp—Gly—OH.HCl (0.05 mmol) (prepared as above mentioned) and H—Lys(Boc)—Pro—Val—Gly—Lys(Boc)—Lys(Boc)—Lys(Boc)—Lys(Boc)—Lys(Boc)—Lys(Boc)—NH$_2$ (0.05 mmol, obtained from the carbobenzoxy derivative by catalytic hydrogenation) in a mixture of dimethylformamide and dimethylsulfoxide (1:1, 3ml) is added N-hydroxysuccinimide (12.7 mg) and triethylamine (0.01 ml). Stirring is continued for 21 hours after an addition of dicyclohexylcarbodiimide (45.4 mg). The reaction mixture is added dropwise to a mixture of ethyl acetate and ether (1:1, 15ml), and the precipitates are collected by filtration, washed, and dried (150 mg). This protected peptide is treated with 90% aqueous trifuloroacetic acid (2 ml) at room temperature for 1 hour in the presence of ethanedithiol (0.1 ml) and anisole (0.15 ml). After an addition of ether (10 ml), the precipitates are collected by filtration, washed, dried (160 mg), and dissolved in 0.1N acetic acid. The solution is applied on a column of Amberlite CG-400 (acetate form, 0.9 × 25 cm). The peptide is eluted with 0.1N acetic acid. The eluate is concentrated, and lyophilized (132 mg). This crude peptide is first purified by carboxymethyl cellulose chromatography (Serva, 0.70 meq/g, 2.2 × 25 cm). Elution is done with an ammonium acetate buffer, pH 6.80, in salt-linear gradient (0.03M—0.06M). Tubes Nos. 101–166 are pooled, concentrated, and lyophilized (81 mg). The obtained peptide is dissolved in a mixture of n-butanol-acetic acid-pyridine-water (12:3:4:6; by volume) and the solution is added on a column of Sephadex G-25 (medium, 2.0 × 75 cm), which equilibrated with the same solvent system. The material which eluted at 2.2 × total column volume (tubes No. 85–130) at the flow rate of 60 ml/hr is collected and lyophilized from water. Yield 71 mg, $[\alpha]_D^{24.5}$ −66.0 ±2.1° (c 0.521, N/10 acetic acid). $\lambda_{max}^{0.1N-NaOH}$ 282 m$\mu$ ($E_{1\%}^{1\ cm}$ 23.9), 289 m$\lambda$ ($E_{1\%}^{1\ cm}$ 22.8), $\lambda_{max}^{0.1N-HCl}$ 280 m$\lambda$ ($E_{1\%}^{1\ cm}$ 21.2), $\lambda_{shoulder}^{0.1N-NCl}$ 288 m$\mu$ ($E_{1\%}^{1\ cm}$ 15.9). Thin layer chromatography gives single spot, and paper electrophoresis revealed to be single component. Amino acid analysis (molar ratio): Lys 6.72 (7), His 1.00 (1), Arg 1.00 (1), Ser 0.91 (1), Glu 1.12 (1), Pro 1.15 (1), Gly 2.00 (2), Aib 1.12 (1), Val 0.96 (1), Met 1.00 (1), Tyr 0.99 (1), Phe 0.95 (1), Trp/Tyr 1.09 (1). (The Figures in the parenthesis mean the theoretical molar ratio.).

What we claim is:

1. A member selected from the group consisting of a compound of the formula:

Aib—Tyr—Ser—Met—Glu—His—Phe—Arg—Trp—Gly—Lys—Pro—Val—Gly—(Lys)$_n$—Y wherein $n$ is an integer of 5–6 and Y is —OH or —HN$_2$ and is bound to the carbonyl group of the C-terminal lysine residue, a non-toxic acid addition salt thereof and a complex thereof.

2. A member selected from the group consisting of Aib—Tyr—Ser—Met—Glu—His—Phe—Arg—Trp—Gly—Lys—Pro—Val—Gly—Lys—Lys—Lys—Lys—Lys—NH$_2$, a non-toxic acid addition salt thereof and a complex thereof.

3. A member selected from the group consisting of Aib—Tyr—Ser—Met—Glu—His—Phe—Arg—Trp—Gly—Lys—Pro—Val—Gly—Lys—Lys—Lys—Lys—Lys—NH$_2$, Aib—Tyr—Ser—Mwet—Glu—His—Phe—Arg—Trp—Gly—Lys—Pro—Val—Gly—Lys—Lys—Lys—Lys—Lys—Lys—NH$_2$, a non-toxic acid addition salt thereof and a complex thereof.

4. A compound according to claim 2 said compound being Aib—Tyr—Ser—Met—Glu—His—Phe—Arg—Trp—Gly—Lys—Pro—Val—Gly—Lys—Lys—Lys—Lys—Lys—NH$_2$.

5. A compound according to claim 3 said compound being Aib—Tyr—Ser—Met—Glu—His—Phe—Arg—Trp—Gly—Lys—Pro—Val—Gly—Lys—Lys—Lys—Lys—Lys—NH$_2$, Aib—Tyr—Ser—Met—Glu—His—Phe—Arg—Trp—Gly—Lys—Pro—Val—Gly—Lys—Lys—Lys—Lys—Lys—Lys—NH$_2$.

* * * * *